(12) United States Patent
Hogenkamp

(10) Patent No.: US 6,335,354 B2
(45) Date of Patent: Jan. 1, 2002

(54) AMINOPYRIDINES AND METHODS OF USING THEREOF

(75) Inventor: Derk J. Hogenkamp, Carlsbad, CA (US)

(73) Assignee: CoCensys Inc., Irvine, CA (US)

( * ) Notice: Subject to any disclaimer, the term of this patent is extended or adjusted under 35 U.S.C. 154(b) by 0 days.

(21) Appl. No.: 09/819,693

(22) Filed: Mar. 29, 2001

Related U.S. Application Data

(60) Provisional application No. 60/193,441, filed on Mar. 31, 2000.

(51) Int. Cl.$^7$ ...................... C07D 213/02; A61K 31/44
(52) U.S. Cl. ........................................ 514/352; 546/307
(58) Field of Search ........................... 546/307; 514/352

(56) References Cited

U.S. PATENT DOCUMENTS

| | | | |
|---|---|---|---|
| 5,945,454 A | 8/1999 | Pevarello et al. | ............ 514/620 |
| 6,211,208 B1 | 4/2001 | Lowe, III | .................... 514/352 |

FOREIGN PATENT DOCUMENTS

| | | | |
|---|---|---|---|
| WO | WO 97/05102 | 2/1997 | |
| WO | WO 00/57877 | 5/2000 | .......... A61K/31/40 |

OTHER PUBLICATIONS

Bensimon, G. et al., "A Controlled Trial of Riluzole in Amyotrophic Lateral Sclerosis." *New Engl. J. Med.* 330:585–591 (1994).
Brown, C.M. et al., "Neuroprotective properties of lifarizine compared with those of other agents in a mouse model of focal cerebral ischaemia," *British J. Pharmacol.* 115:1425–1432 (1995).
Buchan, A.M. et al., "AMPA Antagonists: Do They Hold More Promise for Clinical Stroke Trials Than NMDA Antagonists?," *Stroke Suppl. I* 24:148–152 (1993).
Catterall, W.A., "Neurotoxins that Act on Voltage–Sensitive Sodium Channels in Excitable Membranes," *Ann. Rev. Pharmacol. Toxicol.* 20:15–43 (1980).
Catterall, W.A., "Structure and Function of Voltage–Sensitive Ion Channels," *Science* 242:50–61 (1988).
Catterall, W.A., "Common modes of drug action on Na+ channels: local anesthetics, antiarrhythmics and anticonvulsants," *Trends Pharmacol. Sci.* 8:57–65 (1987).
Creveling, C.R. et al., "Batrachotoxin–Induced Depolarization and [$^3$H]Batrachotoxinin–A 20α–Benzoate Binding in a Vesicular Preparation from Guinea Pig Cerebral Cortex," *Mol. Pharmacol.* 23:350–358 (1983).
Curtin, M.L. et al., "Discovery and Evaluation of a Series of 3–Acylindole Imidazopyridine Platlet–Activating Factor Antagonists," *J. Med Chem.* 41:74–95 (1998).
Denicoff, K.D. et al., "Efficacy of Carbamazepine Compared With Other Agents: A Clinical Practice Survey," *J. Clin. Psychiatry* 55:70–76 (1994).

Dimmock, J.R. et al., "(Aryloxy)aryl Semicarazones and Related Compounds: A Novel Class of Anticonvulsant Agents Possessing High Activity in the Maximal Electroshock Screen," *J. Med Chem.* 39:3984–3997 (1996).
Donaldson, I., "Tegretol: A double blind trial in tinnitus," *Laryngol. Otol.* 95: 947–951 (1981).
Filer, C.N., "The Preparation and Characterization of Tritiated Neurochemicals," Chapter 6 in *Isotopes in the Physical and Biomedical Sciences, vol. 1, Labeled Compounds (Part A)*, pp. 156–192 (1987).
Graham, S.H. et al., "A Dose–Response Study of Neuroprotection Using the AMPA Antagonist NBQX in Rat Focal Cerebral Ischemia," *J. Pharmacol. Exp. Ther.* 276:1–4 (1996).
Graham, S.H. et al., "Neuroprotective Effects of a Use–Dependent Blocker of Voltage–Dependent Sodium Channels, BW619C89, in Rat Middle Cerebral Artery Occlusion," *J. Pharmacol. Exp. Ther.* 269:854–859 (1994).
Hamill, O.P. et al., "Improved Patch–Clamp Techniques for High–Resolution Current Recording from Cells and Cell–Free Membrane Patches," *Pfluegers Arch.* 391:85–100 (1981).
Hunskaar, S. et al., "Formalin test in mice, a useful technique for evaluating mild analgesics," *J. Neurosci. Methods* 14:69–76 (1985).
Iwasaki,Y. et al., "CNQX prevents spinal motor neuron death following sciatic nerve transection in newborn rats," *J. Neurological Sci.* 134:21–25 (1995).

(List continued on next page.)

Primary Examiner—Zinna Northington Davis
(74) Attorney, Agent, or Firm—Sterne, Kessler, Goldstein & Fox PLLC

(57) ABSTRACT

This invention relates to aminopyridines of Formula I:

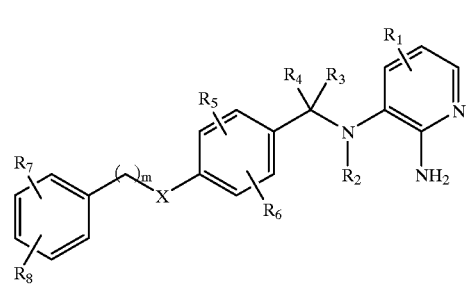

or a pharmaceutically acceptable salt, prodrug or solvate thereof, wherein $R_1$–$R_8$, X and m are set in the specification. The invention is also directed to the use of compounds of Formula I for the treatment of neuronal damage following global and focal ischemia, for the treatment or prevention of neurodegenerative conditions such as amyotrophic lateral sclerosis (ALS), and for the treatment, prevention or amelioration of both acute or chronic pain, as antitinnitus agents, as anticonvulsants, and as antimanic depressants, as local anesthetics, as antiarrhythmics and for the treatment or prevention of diabetic neuropathy.

19 Claims, No Drawings

OTHER PUBLICATIONS

Khanna, I.K. et al., "Facile, Regioselective Synthesis of N–Alkylated 2,3–Diaminopyridines and Imidazo[4,5–b]pyridines," *J. Org. Chem. 60*:960–965 (1995).

Majumdar, B. et al., "An electrocochleographic study of the effects of lignocaine on patients with tinnitus," *Clin. Otolaryngol. 8*: 175–180 (1983).

Møller, A.R., "Similarities Between Chronic Pain and Tinnitus," *Am. J. Otol. 18*:577–585 (1997).

Pevarello, P. et al., "Synthesis of Anticonvulsant Activity of a New Class of 2–[(Arylalkyl)amino]alkanamide Derivatives," *J. Med Chem. 41*:579–590 (1998).

Sheardown, M.J. et al., "AMPA, but not NMDA, receptor antagonism is neuroprotective in gerbil global ischaemia, even when delayed 24 h," *Euro. J. Pharmacol. 236*:347–353 (1993).

Simpson, J.J. et al., "Recent advances in the pharmacological treatment of tinnitus." *Trends Pharmacol. Sci. 20*:12–18 (Jan. 1999).

Stys. P.K. et al., "Ionic Mechanisms of Anoxic Injury in Mammalian CNS White Matter: Role of $Na^+$ Channels and $Na^+$–$Ca^{2+}$ Exchanger," *J. Neurosci. 12*:430–439 (1992).

Taylor, C.P. et al., "Na+ channels as targets for neuroprotective drugs," *Trends Pharmacol. Sci. 16*:309–316 (1995).

Tonndorf, J., "The analogy between tinnitus and pain: A suggestion for a physiological basis of chronic tinnitus," *Hear. Res. 28*:271–275 (1987).

Verdoorn, T.A. et al., "Functional Properties of Recombinant Rat $GABA_A$ Receptors Depend upon Subunit Composition," *Neuron 4*:919–928 (1990).

Wrathall, J.R. et. al., "Amelioration of Functional Deficits from Spinal Cord Trauma with Systemically Adminstered NBQX, and Antagonist of Non–N–methyl–D–aspartate receptors," *Exp. Neurology 137*:119–126 (1996).

Yasushi, J. Biol. Chem. "Specific Inhibition of [$^3$H] Saxitoxin Binding to Skeletal Muscle Sodium Channels by Geographutoxin II, a Polypeptide Channel Blocker" 261:6149–6152 (1986).

PCT International Search Report for International application No. PCT/US01/10125, Jul. 16, 2001.

20 # AMINOPYRIDINES AND METHODS OF USING THEREOF

This application claims the priority benefit under 35 U.S.C. § 119 of U.S. Provisional Appl. No. 60/193,441, filed Mar. 31, 2000, the entirety of which is incorporated by reference herein.

BACKGROUND OF THE INVENTION

1. Field of the Invention

This invention is in the field of medicinal chemistry. In particular, the invention relates to novel aminopyridines, and the discovery that these compounds are anticonvulsants and act as blockers of sodium ($Na^+$) channels.

2. Related Art

Several classes of therapeutically useful drugs including local anesthetics such as lidocaine and bupivacaine, antiarrhythmics such as propafenone and amioclarone, and anticonvulsants such as lamotrigine, phenytoin and carbamazepine, have been shown to share a common mechanism of action by blocking or modulating $Na^+$ channel activity (Catterall, W. A., *Trends Pharmacol. Sci.* 8:57–65 (1987)). Each of these agents is believed to act by interfering with the rapid influx of $Na^+$ ions.

Recently, other $Na^+$ channel blockers such as BW619C89 and lifarizine have been shown to be neuroprotective in animal models of global and focal ischemia and are presently in clinical trials (Graham el al., *J. Pharmacol. Exp. Ther.* 269:854–859 (1994); Brown et al., *British J. Pharmacol.* 115:1425–1432 (1995)).

The neuroprotective activity of $Na^+$ channel blockers is due to their effectiveness in decreasing extracellular glutamate concentration during ischemia by inhibiting the release of this excitotoxic amino acid neurotransmitter. Studies have shown that unlike glutamate receptor antagonists, $Na^+$ channel blockers prevent hypoxic damage to mammalian white matter (Stys et al., *J. Neurosci.* 12:430–439 (1992)). Thus, they may offer advantages for treating certain types of strokes or neuronal trauma where damage to white matter tracts is prominent.

Another example of clinical use of a $Na^+$ channel blocker is riluzole. This drug has been shown to prolong survival in a subset of patients with ALS (Bensimm et al., *New Engl. J. Med.* 330:585–591 (1994)) and has subsequently been approved by the FDA for the treatment of ALS. In addition to the above-mentioned clinical uses, carbamazepine, lidocaine and phenytoin are occasionally used to treat neuropathic pain, such as from trigeminal neurologia, diabetic neuropathy and other forms of nerve damage (Taylor and Meldrum, *Trends Pharmacol. Sci.* 16:309–316 (1995)), and carbamazepine and lamotrigine have been used for the treatment of manic depression (Denicott el al., *J. Clin. Psychiatry* 55: 70–76 (1994)). Furthermore, based on a number of similiarities between chronic pain and tinnitus, (Moller, A. R. *Am. J. Otol.* 18: 577–585 (1997); Tonndorf, *J. Hear. Res.* 28. 271–275 (1987)) it has been proposed that tinnitus should be viewed as a form of chronic pain sensation (Simpson, J. J. and Davies, E. W. *Tip.* 20: 12–18 (1999)). Indeed, lignocaine and carbamazepine have been shown to be efficacious in treating tinnitus (Majumdar, B. et al. *Clin. Otolaryngol.* 8: 175–180 (1983); Donaldson, I. *Laryngol. Otol.* 95: 947–951 (1981)).

It has been established that there are at least five to six sites on the voltage-sensitive $Na^+$ channels which bind neurotoxins specifically (Catterall, W. A., *Science* 242:50–61 (1988)). Studies have further revealed that therapeutic antiarrhythmics, anticonvulsants and local anesthetics whose actions are mediated by $Na^+$ channels, exert their action by interacting with the intracellular side of the $Na^+$ channel and allosterically inhibiting interaction with neurotoxin receptor site 2 (Catterall, W. A., *Ann. Rev. Pharmacol. Toxicol.* 10:15–43 (1980)).

SUMMARY OF THE INVENTION

The present invention is related to the discovery that aminopyridines represented by Formula I are anticonvulsants and act as blockers of sodium ($Na^+$) channels.

The invention is also related with treating a disorder responsive to the blockade of sodium channels in a mammal suffering from excess activity of said channels by administering an effective amount of a compound of Formula I as described herein.

The present invention is also directed to the use of a compound of Formula I for the treatment of neuronal damage following global and focal ischemia, and for the treatment or prevention of neurodegenerative conditions such as amyotrophic lateral sclerosis (ALS), for the treatment of tinnitus, as antimanic depressants, as local anesthetics, as antiarrhythmics, as anticonvulsants and for the treatment or prevention of diabetic neuropathy and for the treatment of pain including both acute and chronic pain and migraine headache.

One aspect of the present invention is directed to the novel aminopyridines of Formula I.

Another aspect of the present invention is directed to the novel compounds of Formula I as blockers of sodium channels.

A further aspect of the present invention is to provide a method for treating, preventing or ameliorating neuronal loss following global and focal ischemia; treating, preventing or ameliorating pain including acute and chronic pain, and neuropathic pain; treating, preventing or ameliorating convulsion and neurodegenerative conditions; treating, preventing or ameliorating manic depression; using as local anesthesics and anti-arlhythmics, and treating tinnitus by administering a compound of Formula I to a mammal in need of such treatment or use.

Also, an aspect of the present invention is to provide a pharmaceutical composition useful for treating disorders responsive to the blockade of sodium ion channels, containing an effective amount of a compound of Formula I in a mixture with one or more pharmaceutically acceptable carriers or diluents.

Further, the present invention is directed to $^3H$ and $^{14}C$ radiolabeled compounds of Formula I and their use as radioligands for their binding site on the sodium channel.

Additional embodiments and advantages of the invention will be set forth in part in the description that follows, and in part will be obvious from the description, or may be learned by practice of the invention. The embodiments and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF THE INVENTION

The present invention arises out of the discovery that aminopyridines of Formula I act as blockers of $Na^+$ channels. In view of this discovery compounds of Formula I are useful for treating disorders responsive to the blockade of sodium ion channels.

The compounds useful in this aspect of the present invention are aminopyridines represented by Formula I:

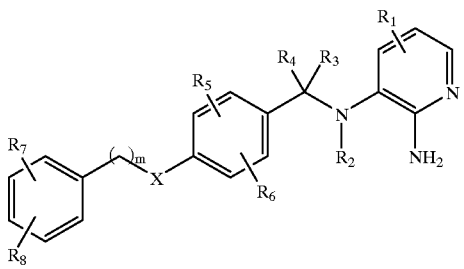

I or a pharmaceutically acceptable salt, prodrug or solvate thereof, wherein:

R$_1$ is selected from the group consisting of hydrogen, alkyl, alkenyl, alkynyl, halogen, haloalkyl, cycloalkyl, amino, aminoalkyl, hydroxyalkyl, alkoxyalkyl, alkoxy, alkylthio, alkylsulfinyl, alkylsulfonyl, carboxyalkyl, cyano, alkylamino, aminocarbonyl, alkylaminocarbonyl, arylaminocarbonyl, aralkylaminocarbonyl, alkylcarbonylamino, arylcarbonylamino, alkylcarbonyl, heterocyclocarbonyl, aminosulfonyl, alkylaminosulfonyl, and heterocyclosulfonyl, all of which can be optionally substituted;

R$_2$ is hydrogen or C$_{1-6}$ alkyl and R$_3$ is hydrogen, or R$_2$ and R$_3$ together form a bond;

R$_4$ is hydrogen or C$_{1-6}$ alkyl;

R$_5$, R$_6$, R$_7$, and R$_8$ are independently selected from the group consisting of hydrogen, alkyl, alkenyl, alkynyl, halogen, haloalkyl, hydroxyalkyl, hydroxy, nitro, amino, aminoalkyl, cyano, amide, carboxyalkyl, alkoxyalkyl. ureido, acylamino, thiol, acyloxy, azido, alkoxy, carboxy, carbonylamido and alkylthiol;

X is one of O, S, NR$_9$, or CH$_2$, wherein R$_9$ is hydrogen or alkyl; and m is 0–3.

Preferably X is O or S, more preferably X is O.

One group of preferred compounds useful in the present invention are aminopyridines represented by Formula II:

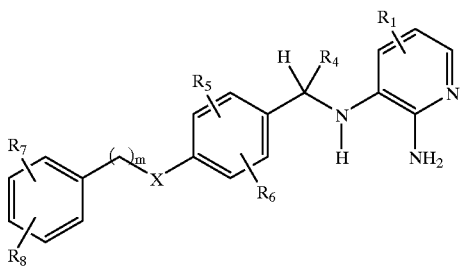

II a pharmaceutically acceptable salt, prodrug or solvate thereof, wherein:

R$_1$, R$_4$–R$_8$ are as defined above, X is O or S and m is 0 or 1.

Preferably, R$_1$ is selected from the group consistinlg of hydrogen, C$_1$–C$_6$ alkyl, C$_2$–C$_6$ alkenyl, C$_2$–C$_6$ alkynyl, amino(C$_1$–C$_6$)alkyl, amino, C$_1$–C$_6$ alkylthio, cyano, C$_1$–C$_6$ alkylsulfinyl, hydroxy(C$_1$–C$_6$)alkyl, C$_1$–C$_6$ alkoxy, aminocarbonyl, C$_1$–C$_6$ alkylaminocarbonyl, C$_6$–C$_{10}$ arylaminocarbonyl, C$_6$–C$_{10}$ aryl(C$_1$–C$_6$) alkylaminocarbonyl, C$_1$–C$_6$ alkylcarbonylamino, C$_6$–C$_{10}$ arylcarbonylamino, C$_6$–C$_{10}$ aryl(C$_1$–C$_6$) alkylcarbonylamino, C$_1$–C$_6$ alkylcarbonyl, heterocyclocarbonyl, aminosulfonyl, C$_1$–C$_6$ alkylaminosulfonyl, C$_1$–C$_6$ alkylsulfonyl, and heterocyclosulfonyl, more preferably hydrogen, C$_1$–C$_6$ alkyl, C$_1$–C$_6$ alkoxy, amino(C$_1$–C$_6$)alkyl, C$_1$–C$_6$ alkylthio and aminocarbonyl. Suitable heterocycles in the heterocycle-containing groups include, for example, N-morpholinyl, N-pyrrolidinyl and N-piperazinyl.

Preferably, R$_5$, R$_6$, R$_7$, and R$_8$ are independently selected from the group consisting of hydrogen, halo, C$_1$–C$_6$ haloalkyl, C$_6$–C$_{10}$ aryl, C$_4$–C$_7$ cycloalkyl, C$_1$–C$_6$ alkyl, C$_2$–C$_6$ alkenyl, C$_2$–C$_6$ alkynyl, C$_6$–C$_{10}$ aryl(C$_1$–C$_6$)alkyl, C$_6$–C$_{10}$ aryl(C$_2$–C$_6$)alkenyl, C$_6$–C$_{10}$ aryl(C$_2$–C$_6$)alkynyl, C$_1$–C$_6$ hydroxyalkyl, nitro, amino, ureido, cyano, C$_1$–C$_6$ acylamido, hydroxy, thiol, C$_1$–C$_6$ acyloxy, azido, C$_1$–C$_6$ alkoxy, or carboxy. Halo is preferably fluoro or chloro. The groups R$_5$–R$_8$ each take the place of a hydrogen atom that would otherwise be present in any position on the aryl ring to which the R group is attached. Especially preferred are compounds where R$_5$ and R$_6$ are both hydrogen, R$_7$ is hydrogen and R$_8$ is a fluoro in the meta- or para-position.

Since the compounds of Formula I are blockers of sodium (Na$^+$) channels, a number of diseases and conditions mediated by sodium ion influx can be treated employing these compounds. Therefore, the invention is related to a method of treating, preventing or ameliorating neuronal loss associated with stroke, global and focal ischemia, CNS trauma, hypoglycemia and surgery, spinal cord trauma; as well as treating or ameliorating neurodegenerative diseases including Alzheimer's disease, amyotrophic lateral sclerosis, Parkinson's disease, treating or ameliorating anxiety, convulsions, glaucoma, migraine headache, and muscle spasm. The compounds of Formula I are also useful as antitinnitus agents, antimanic depressants, as local anesthetics, and as antiarrhythmics; as well as for treating, preventing or ameliorating pain including surgical, chronic and neuropathic pain. In each instance, the methods of the present invention require administering to an animal in need of such treatment an effective amount of a sodium channel blocker of the present invention, or a pharmaceutically acceptable salt or prodrug thereof.

Exemplary preferred compounds that may be employed in this method of invention include, without limitation:

N$^3$-[4-(3-fluorobenzyloxy)benzyl]pyridine-2,3-diamine;

N$^3$-[4-(3-fluorobenzyloxy)benzyl]denelpyridine-2,3-diamine;

N$^3$-[4-(4-fluorophenoxy)benzyl]pyridine-2,3-diamine; and

N$^3$-[4-(4-fluorophenoxy)benzylidene]pyridine-2,3-diamine.

Useful aryl groups are C$_{6-14}$ aryl, especially C$_{6-10}$ aryl. Typical C$_{6-14}$ aryl groups include phenyl, naphthyl, phenanthryl, anthracyl, indenyl, azulenyl, biphenyl, biphenylenyl and fluorenyl groups.

Useful cycloalkyl groups are C$_{3-8}$ cycloalkyl. Typical cycloalkyl groups include cyclopropyl, cyclobutyl, cyclopentyl, cyclohexyl and cycloheptyl.

Useful halo or halogen groups include fluorine, chlorine, bromine and iodine.

Useful alkyl groups include straight-chained and branched C$_{1-10}$ alkyl groups, more preferably C$_{1-6}$ alkyl groups. Typical C$_{1-10}$ alkyl groups include methyl, ethyl, propyl, isopropyl. butyl, sec-butyl, lert-butyl, 3-pentyl, hexyl and octyl groups. Also contemplated is a trimethylene group substituted on two adjoining positions on the benzene ring of the compounds of the invention.

Useful alkenyl groups are $C_{2-6}$ alkenyl groups, preferably $C_{2-4}$ alkenyl. Typical $C_{2-4}$ alkenyl groups include ethenyl, propenyl, isopropenyl, butenyl, and sec-butenyl.

Useful alkynyl groups are $C_{2-6}$ alkynyl groups, preferably $C_{2-4}$ alkynyl. Typical $C_{2-4}$ alkynyl groups include ethynyl, propynyl, butynyl, and 2-butynyl groups.

Useful arylalkyl groups include any of the above-mentioned $C_{1-10}$ alkyl groups substituted by any of the above-mentioned $C_{6-14}$ aryl groups. Useful values include benzyl, phenethyl and naphthylmethyl.

Useful arylalkenyl groups include any of the above-mentioned $C_{2-4}$ alkenyl groups substituted by any of tile above-mentioned $C_{6-14}$ aryl groups.

Useful arylalkynyl groups include any of the above-mentioned $C_{2-4}$ alkynyl groups substituted by any of the above-mentioned $C_{6-14}$ aryl groups. Useful values include phenylethynyl and phenylpropynyl.

Useful cycloalkylalkyl groups include any of the above-mentioned $C_{1-10}$ alkyl groups substituted by any of the above-mentioned cycloalkyl groups.

Useful haloalkyl groups include $C_{1-10}$ alkyl groups substituted by one or more fluorine, chlorine, bromine or iodine atoms, e.g. fluoromethyl, difluoromethyl, trifluoromethyl, pentafluoroethyl, 1,1-difluoroethyl and trichloromethyl groups.

Useful hydroxyalkyl groups include $C_{1-10}$ alkyl groups substituted by hydroxy, e.g. hydroxymethyl, hydroxyethyl, hydroxypropyl and hydroxybutyl groups.

Useful alkoxy groups include oxygen substituted by one of the $C_{1-10}$ alkyl groups mentioned above.

Useful alkylthio groups include sulfur substituted by one of the $C_{1-10}$ alkyl groups mentioned above.

Useful acylamino groups are any acyl group, particularly $C_{2-6}$ alkanoyl or $C_{6-10}$ aryl($C_{2-6}$)alkanoyl attached to an amino nitrogen, e.g. acetamido, propionamido, butanoylamido, pentanoylamido, hexanoylamido, and benzoyl.

Useful acyloxy groups are any $C_{1-6}$ acyl (alkanoyl) attached to an oxy (—O—) group, e.g. acetoxy, propionoyloxy, butanoyloxy, pentanoyloxy, hexanoyloxy and the like.

The term heterocyclic is used herein to mean saturated or wholly or partially unsaturated 3–7 membered monocyclic, or 7–10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable Examples include, but are not limited to, pyrrolidine, piperidine, piperazine, morpholine, imidazoline, pyrazolidine, benzodiazepines, and the like.

Useful heterocycloalkyl groups include any of the above-mentioned $C_{1-10}$ alkyl groups substituted by any of the above-mentioned heterocyclic groups.

Useful alkylamino and dialkylamino groups are —$NHR_{10}$ and —$NR_{10}R_{11}$, wherein $R_{10}$ and $R_{11}$ are $C_{1-10}$ alkyl groups.

Aminocarbonyl group is —$C(O)NH_2$.

Useful alkylaminocarbonyl groups are carbonyl groups substituted by —$NHR_{10}$ and —$NR_{10}R_{11}$, wherein $R_{10}$ and $R_{11}$ are $C_{1-10}$ alkyl groups. Useful alkylthiol groups include any of the above-mentioned $C_{1-10}$ alkyl groups substituted by a —SH group.

A carboxy group is —COOH.

An azido group is —$N_3$.

An ureido group is —NH—C(O)—$NH_2$.

An amino group is —$NH_2$.

An amide group is an organic radical having —NHC(O)— as a functional group.

Optional substituents on $R_1$ include any one of halo, halo($C_{1-6}$)alkyl, aryl, heterocycle, cycloalkyl, $C_{1-6}$ alkyl, $C_{2-6}$ alkenyl, $C_{2-6}$ alkynyl, aryl($C_{1-6}$)alkyl, aryl($C_{2-6}$)alkenyl, aryl($C_{2-6}$)alkynyl, cycloalkyl($C_{1-6}$)alkyl, heterocyclo($C_{1-6}$)alkyl, hydroxy($C_{1-6}$)alkyl, amino($C_{1-6}$)alkyl, carboxy($C_{1-6}$)alkyl, alkoxy($C_{1-6}$)alkyl, nitro. amino, ureido, cyano, acylamino, hydroxy, thiol, acyloxy, azido, alkoxy, carboxy, aminocarbonyl, and $C_{1-6}$ alkylthiol groups mentioned above. Preferred optional substituents include: halo, halo($C_{1-6}$)alkyl, hydroxy($C_{1-6}$)alkyl, amino($C_{1-6}$)alkyl, hydroxy, nitro, $C_{1-6}$ alkyl, alkoxy and amino.

The invention disclosed herein is meant to encompass all pharmaceutically acceptable salts thereof of the disclosed compounds. The pharmaceutically acceptable salts include, but are not limited to, metal salts such as sodium salt, potassium salt, secium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate, and the like; amino acid salts such as arginate, asparginate, glutamate and the like.

The invention disclosed herein is also meant to encompass prodrugs of the disclosed compounds. Prodrugs are considered to be any covalently bonded carriers which release the active parent drug in vivo.

The invention disclosed herein is also meant to encompass the in vivo metabolic products of the disclosed compounds. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled compound of the invention, administering it parenterally in a detectable dose to an animal such as rat, mouse, guinea pig, monkey, or to man, allowing sufficient time for metabolism to occur and isolating its conversion products from the urine, blood or other biological samples.

The invention disclosed herein is also meant to encompass the disclosed compounds being isotopically-labelled by having one or more atoms replaced by an atom having a different atomic mass or mass number.

Examples of isotopes that can be incorporated into the disclosed compounds include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Some of the compounds disclosed herein may contain one or more asymmetric centers and my thus give rise to enantiomers, diastercomers, and other stereoisomeric forms.

The present invention is also meant to encompass all such possible forms as well as their racemic and resolved forms and mixtures thereof. When the compounds described herein contain olefinic double bonds or other centers of geometric asymmetry, and unless specified otherwise, it is intended to include both E and Z geometric isomers. All tautomers are intended to be encompassed by the present invention as well.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule.

The invention is also directed to a method for treating disorders responsive to the blockade of sodium channels in animals suffering thereof. Particular preferred embodiments of the aminopyridine compounds for use in method of this invention are represented by previously defined Formulae I–II.

The compounds of this invention may be prepared using methods known to those skilled in the art. Aminopyridine derivatives according to the invention can be prepared, for example, as illustrated by examplary reactions in Scheme 1. Formation of the aryl substituted aminopyridine was accomplished as described by Cuilin, M. L. et al. (*J. Med. Chem.* 41:74–95 (1998)) and Khanna, l. K. et al. (*J. Org. Chem.* 60: 960–965 (1995)).

Scheme 1

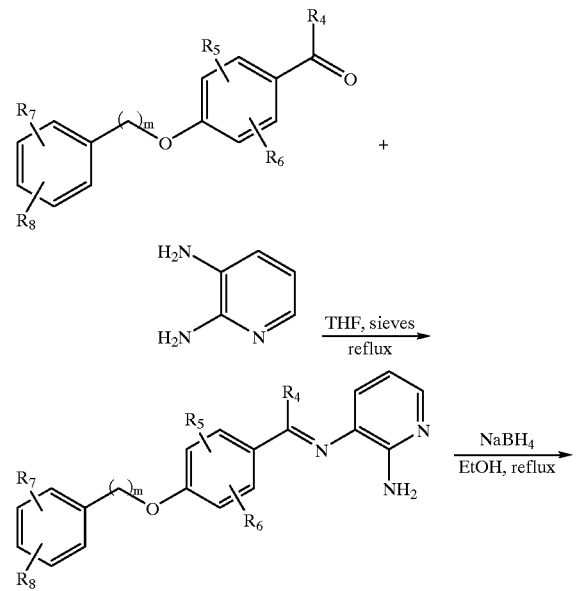

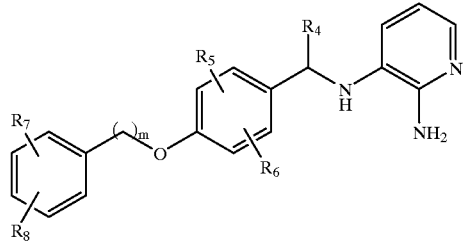

wherein $R_4$–$R_8$ are as defined above. Suitable methods for preparing different aldehyde and ketone starting compounds are described, for example, in U.S. Provisional Patent Application No. 60/188,188, filed Mar. 10, 2000, and U.S. Non-Provisionial Patent Application No. 09/533,864, filed Mar. 24, 2000 (Attorney Ref:1483.0360001). Other suitable methods are described by Dimmock et al. (*J. Med. Chem.* 39: 3984–3997 (1996)) and Pevarello et al. (*J. Med. Chem.* 41: 579–590 (1998)).

The compounds of the present invention were assessed by electrophysiological assays in dissociated hippocampal neurons for sodium channel blocker activity. These compounds also could be assayed for binding to the neuronal voltage-dependent sodium channel using rat forebrain membranes and [$^3$H]BTX-B.

Sodium channels are large transmembrane proteins that are expressed in various tissues. They are voltage sensitive channels and are responsible for the rapid increase of $Na^+$ permeability in response to depolarization associated with the action potential in many excitable cells including muscle, nerve and cardiac cells.

One aspect of the present invention is the discovery of the mechanism of action of the compounds herein described as specific $Na^+$ channel blockers. based upon the discovery of this mechanism, these compounds are contemplated to be useful in treating or preventing neuronal loss due to local or global ischemia, and in treating or preventing neurodegenerative disorders including ALS, anxiety, and epilepsy. They are also expected to be effective in treating, preventing or ameliorating neuropathic pain, surgical pain, chronic pain and tinnitus. The compounds are also expected to be useful as antiarrhythmics, anesthetics and antimanic depressants.

The present invention is directed to compounds of Formulae I–II that are blockers of voltage-sensitive sodium channels. According to the present invention, those compounds having preferred sodium channel blocking properties exhibit an $IC_{50}$ of about 100 µM or less in the electrophysiological assay described herein. Preferably, the compounds of the present invention exhibit an $IC_{50}$ of 10 µM or less. Most preferably, the compounds of the present invention exhibit an $IC_{50}$ of about 1.0 µM or less. Substituted heteroaryl compounds of the present invention may be tested for their $Na^+$ channel blocking activity by the following electrophysiological and binding assays.

The invention is also directed to $^3$H and $^{14}$C radiolabeled compounds of Formula I and their use as radioligands for their binding site on the sodium channel. For example, one use of the labeled compounds of the invention is the characterization of specific receptor binding. Another use of the labeled compounds of the invention is an alternative to animal testing for the evaluation of stiucture-activity relationships. The receptor assay is performed at a fixed concentration of a labeled compound of Formula I and at increasing concentrations of a test compound in a competition assay.

Tritiated compounds of Formula I can be prepared by introducing tritium into the compound of Formula I by, for example, catalytic dehalogenation with tritium. This method includes reacting a suitably halogen-substituted precursor of a compound of Formula I with tritium gas in the presence of a suitable catalyst, for example Pd/C, in the presence or absence of a base. Other suitable methods for preparing tritiated compounds can be found in Filer, *Isotopes in the Physical and Biomedical Sciences*, Vol. 1, *Labeled Compounds* (Part A), Chapter 6. $^{14}$C-labeled compounds can be prepared by employing starting materials having a $^{14}$C carbon.

Electrophysiological Assay:

Cell preparation. HEK-293 cells stably expressing the hSkM1 isoform of $Na^+$ channels (generous gift from Dr. A. L. George, Vanderbilt University Medical School) were cultured using standard techniques, as described previously (Verdoorn, T. A, et al., *Neuron* 4:919–928 (1990)). For electrophysiology, cells were plated onto 35 mm Petri dishes (pre-coated with poly-D-lysine) at a density of 1:40 on the day of re-seeding from confluent cultures. Our experience has been that cells are suitable for recordings for 2–3 days after plating.

Patch-clamp recordings of voltage-sensitive $Na^+$ currents. Whole-cell voltage-clamp recordings were made using conventional patch-clamp techniques (Hamill et al, *Pfluegers Arch*. 391:85–100 (1981)) with an Axopatch 200A amplifier (Axon Instruments, Foster City, Calif.). Recordings were made within 2–3 hours after neuron dissociation. The recording chamber was continuously superfused with the external solution (150 mM NaCl, 5.4 mM KCl, 1.8 mM $CaCl_2$, 1 mM $MgCl_2$, 10 mM HEPES, 10 mM glucose, pH 7.4 (NaOH)) at a speed of about 1 mL/min. Recording pipettes were pulled from thick-walled capillaries (WPI, Sarasota, Fla.) and fire-polished. The pipette resistances ranged from 1 to 3 MΩ when the pipettes were filled with internal solution containing (in mM): 110 CsF, 10 NaCl, 5 $MgCl_2$, 11 EGTA, 10 HEPES, pH adjusted to 7.4 with CsOH. Osmolality was set with a difference of 15–20 mmol/kg between external and internal solutions (lower inside the cell). Drugs and intervening wash-outs were applied through a linear array of flow pipes (Drummond Microcaps, 2 $\mu$L, 64-mm length). Compounds are dissolved in dimethylsulfoxide (DMSO) to make a 30 mM stock solution, which was subsequently diluted into the external solution to give final concentrations of 0.1–100 $\mu$M. At the highest (1%) concentration, DMSO inhibited the size of Nat current only slightly. Currents were recorded at room temperature (22–25° C.), filtered at 5 kHz with an active 8-pole Bessel filter (Frequency Devices, Haverhill, Mass.), digitized at 10–50 $\mu$s intervals, and stored using Digidata 1200 analog/digital interface with Pclamp6/Clampex software (Axon Instruments). Series resistance was cancelled typically by ~75% when necessary. The inhibitory potency of drugs was assessed by measuring reductions in the peak amplitude of $Na^+$ currents induced by increasing concentrations of compounds tested. $Na^+$ currents were elicited by stepping membrane voltage from holding potentials over the range −100 mV to −50 mV, to a pulse potential of −10 mV. The test pulse duration was 5–10 msec, repeated at a frequency ≦1 Hz. Concentration-inhibition curves were fitted with equation 1:

$$I/I_{control} = 1/(1+([compound]/IC_{50})) \qquad \text{Eq. 1}$$

where $I_{control}$ is the maximal $Na^+$ current in the absence of antagonist, [compound] is the drug concentration, and $IC_{50}$ is the concentration of compound that produces half maximal inhibition.

In vitro Binding Assay:

The ability of compounds of the present invention to modulate either site 1 or site 2 of the $Na^+$ channel was determined following the procedures fully described in Yasushi, *J. Biol. Chem.* 261:6149–6152 (1986) and Creveling, *Mol. Pharmacol.* 23:350–358 (1983), respectively. Rat forebrain membranes were used as sources of $Na^+$ channel proteins. The binding assays were conducted in 130 $\mu$M choline chloride at 37° C. for 60-minute incubation with [$^3$H] saxitoxin and [$^3$H] batrachotoxin as radioligands for site 1 and site 2, respectively.

In vivo Pharmacology:

The compounds of the present invention may be tested for in vivo anticonvulsant activity after i.v., p.o. or i.p. injection using a number of anticonvulsant tests in mice, including the maximum electroshock seizure test (MES). Maximum electroshock seizures were induced in male NSA mice weighing between 15–20 g and male Sprague-Dawley rats weighing between 200–225 g by application of current (50 mA, 60 pulses/sec, 0.8 msec pulse width, 1 sec duration, D.C., mice; 99 mA. 125 pulses/sec, 0.8 msec pulse width, 2 sec duration, D.C., rats) using a Ugo Basile FCT device (Model 7801). Mice were restrained by gripping the loose skin on their dorsal surface and saline-coated corneal electrodes were held lightly against the two corneae. Rats were allowed free movement on the bench top and ear-clip electrodes were used. Current was applied and animals were observed for a period of up to 30 seconds for the occurrence of a tonic hindlimb extensor response. A tonic seizure was defined as a hindlimb extension in excess of 90 degrees from the plane of the body. Results were treated in a quantal manner.

The compounds may be tested for their antinociceptive activity in the formalin model as described in Hunskaar, S., O. B. Fasmer, and K. Hole, *J. Neurosci. Methods* 14: 69–76 (1985). Male Swiss Webster NIH mice (20–30 g; Harlan, San Diego, Calif.) were used in all experiments. Food was withdrawn on the day of experiment. Mice were placed in Plexiglass jars for at least 1 hour to accommodate to the environment. Following the accommodation period mice were weighed and given either the compound of interest administered i.p. or p.o., or the appropriate volume of vehicle (10% Tween-80). Fifteen minutes after the i.p. dosing, and 30 minutes after the p.o. dosing mice were injected with formalin (20 $\mu$L of 5% formaldehyde solution in saline) into the dorsal surface of the right hind paw. Mice were transferred to the Plexiglass jars and monitored for the amount of time spent licking or biting the injected paw. Periods of licking and biting were recorded in 5 minute intervals for 1 hour after the formalin injection. All experiments were done in a blinded manner during the light cycle. The early phase of the formalin response was measured as licking/biting between 0–5 minutes, and the late phase was measured from 15–50 minutes. Differences between vehicle and drug treated groups were analyzed by one-way analysis of variance (ANOVA). A P value ≦0.05 was considered significant. Having activity in blocking the acute and second phase of formalin-induced paw-licking activity, the compounds are considered to be efficacious for acute and chronic pain.

The compounds may be tested for their potential for the treatment of chronic pain (antiallodynic and antihyperalgesic activities) in the Chung model of peripheral neuropathy. Male Sprague-Dawley rats weighing between 200–225 g were anesthetized with halothane (1–3% in a mixture of 70% air and 30% oxygen) and their body temperature controlled during anesthesia through use of a homeothermic blanket. A 2-cm dorsal midline incision was then made at the L5 and L6 level and the para-vertibral muscle groups retracted bilaterally. L5 and L6 spinal nerves were then be exposed, isolated, and tightly ligated with 6-0 silk suture. A sham operation was performed exposing the contralateral L5 and L6 spinal nerves as a negative control.

Tactile Allodynia: Rats were transferred to an elevated testing cage with a wire mesh floor and allowed to acclimate for five to ten minutes. A series of Semmes-Weinstein monofilamenits were applied to the plantar surface of the hinidpaw to determine the animal's withdrawal threshold. The first filament used possessed a buckling weight of 9.1 (ms (0.96 log value) and was applied up to five times to see if it elicited a withdrawal response. If the animal had a withdrawal response then the next lightest filament in the series would be applied up to five times to determine if it could elicit a response. This procedure was repeated with subsequent lesser filaments until there was no response and the lightest filament that elicited a response was recorded. If the animal did not have a withdrawal response from the initial 9.1 gms filament then subsequent filaments of increased weight were applied until a filament elicited a response and this filament was then recorded. For each animal, three measurements were made at every time point to produce an average withdrawal threshold determination. Tests were performed prior to and at 1, 2, 4 and 24 hours post drug administration. Tactile allodynia and mechanical hyperalgesia tests were conducted concurrently.

Mechanical Hyperalgesia: Rats were transferred to an elevated testing cage with a wire mesh floor and allowed to acclimate for five to ten minutes. A slightly blunted needle was touched to the plantar surface of the hindpaw causing a dimpling of the skin without penetrating the skin. Administration of the needle to control paws typically produced a quick flinching reaction, too short to be timed with a stopwatch and arbitrarily given a withdrawal time of 0.5 second. The operated side paw of neuropathic animals exhibited an exaggerated withdrawal response to the blunted needle. A maximum withdrawal time of ten seconds was used as a cutoff time. Withdrawal times for both paws of the animals were measured three times at each time point with a five-minute recovery period between applications. The three measures were used to generate an average withdrawal time for each time point. Tactile allodynia and mechanical hyperalgesia tests were conducted concurrently.

The compounds may be tested for their neuroprotective activity after focal and global ischemia produced in rats or gerbils according to the procedures described in Buchan el al (*Stroke*, Suppl. 148–152 (1993)) and Sheardown et al. (*Eur. J. Pharmacol.* 236:347–353 (1993)) and Graham el al. (*J. Pharmacol. Exp. Therap.* 276:1–4 (1996)).

The compounds may be tested for their neuroprotective activity after traumatic spinal cord injury according to the procedures described in Wrathall et al. (*Exp. Neurology* 137:119–126 (1996)) and Iwasaki el al. (*J. Neuro Sci.* 134:21–25 (1995)).

Compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for epilepsy, neurodegenerative diseases, anesthetic, arrhythmia, manic depression, and pain. For intramuscular injection, the dose is generally about one-half of the oral dose.

In the method of treatment or prevention of neuronal loss in global and focal ischemia, brain and spinal cord trauma, hypoxia, hypoglycemia, status epilepsy and surgery, the compound can be administrated by intravenous injection at a dose of about 0.025 to about 10 mg/kg.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular heteroaryl compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts are formed by mixing a solution of the heteroaryl compound of the present invention with a solution of a pharmaceutically acceptable non-toxic base such as sodium hydroxide, potassium hydroxide, choline hydroxide, sodium carbonate and the like.

The pharmaceutical compositions of the invention may be administered to any animal that may experience the beneficial effects of the compounds of the invention. Foremost among, such animals are mammals, e.g., humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings that, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations, which can be used rectally, include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension, and include, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

$N^3$-[4-(3-Fluorobenzyloxy)benzyl]pyridine-2,3-diamine a) 4-(3-Fluorobenzyloxy)benizaldehyde: A mixture of 4-hydroxybenzaldehyde (3.1 g, 24.8 mmol) 3-fluorobenzylchloride (2.4 mL, 19.8 mmol), potassium carbonate (74.5 mmol), and catalytic sodium iodide in ethanol was refluxed for several hours. The reaction was monitored by TLC. When the reaction was complete, the mixture was cooled to room temperature, and partitioned between ethyl acetate and an aqueous sodium hydroxide solution (2N). The separated organic layer was washed one more time with an aqueous sodium hydroxide solution (2N), dried over sodium sulfate, filtered and evaporated under reduced pressure to give the product as a yellow oil. This material was carried on without further purification. $^1$H NMR (CDCl$_3$): δ 9.89 (s, 1H), 7.84 (d, J=8.7 Hz, 2H), 7.4–7.1 (m, 4H), 7.07 (d, J=9.0 Hz, 2H), 5.15 (s, 2H).

b) $N^3$-[4-(3-Fluorobenzyloxy)benzylidene]pyridine-2,3-diamine: A mixture of 4-(3-fluorobenzyloxy)benzaldehyde (0.51 g, 2.2 mmol), 2,3-diaminopyridine (0.33 g, 2.96 mmol), dried molecular sieves (4 Å, 2.1 g) in THF was refluxed for 5 hours, then stirred at room temperature overnight. The mixture was filtered and the filtrate was evaporated under reduced pressure to give a yellow solid. The crude product was purified by column chromatography affording 448 mg (63%) of the product as a yellow solid. $^1$H NMR (CDCl$_3$): δ 8.44 (s, 1H), 7.95 (dd, J=5.1, 1.5 Hz, 1H), 7.86 (d, J=8.7 Hz, 2H), 7.40–7.33 (m, 1H), 7.22–7.15 (m, 3H), 7.06–7.01 (m, 3H), 6.66 (dd, J=7.5, 4.8 Hz, 1H), 5.14 (s, 2H), 4.96 (bs, 2H).

c) $N^3$-[4-(3-Fluorobenzyloxy)benzyl]pyridine-2,3-diamine: A mixture of $N^3$-[4-(3-fluorobenzyloxy)benzylidene]pyridine-2,3-diamine (0.4 g, 1.24 mmol), and sodium borohydride (0.48 g, 12.4 mmol) in ethanol was refluxed overnight. Ihe solution was cooled to room temperature, then partitioned between ethyl acetate and water. The organic layer was dried over sodium sulfate, filtered, and evaporated under reduced pressure to give a yellow oil. The oil was purified by column chromatography to give 287 mg (72%) of the final product as a yellow solid, mp 91–93 ° C. $^1$H NMR (CDCl$_3$): δ 7.61 (d, J=5.1 Hz, 1H), 7.38–7.26 (m, 1H), 7.30 (d, J=8.4 Hz, 2H), 7.20–7.14 (m, 2H), 7.04–6.93 (m, 3H), 6.82 (d, J=7.8 Hz, 1H), 6.68 (dd, J=5.1, 7.2 Hz, 1H), 5.06 (s, 2H), 4.22 (d, J=4.8 Hz, 2H), 4.20 (bs, 2H), 3.49 (bs, 1H).

EXAMPLE 2

$N^3$-[4-(4-Fluorophenoxy)benzyl]pyridine-2,3-diamine $N^3$-[4-(4-Fluorophenoxy)benzyl]pyridine-2,3-diamine was prepared by the method of Example 1 starting with 4-(4-fluorophenoxy)benzaldehyde. $^1$H NMR (CDCl$_3$): δ 7.63 d, J=5.1 Hz, 1H), 7.33 (d, J=8.4 Hz, 2H), 7.06–6.94 (m, 1H), 6.82 (d, J=6.6 Hz, 1H), 6.69 (dd, J=4.8, 7.2 Hz, 1H), 4.26 (d, J=5.1 Hz, 1H), 4.18 (bs, 2H), 3.51 (bs, 1H); mp 117–118° C.

EXAMPLE 3

$N^3$-[4-(4-Fluorophenoxy)benzyl]pyridine-2,3-diamine as Anticonvulsant

The ability of $N^3$-[4-(4-fluorophenoxy)benzyl]pyridine-2,3-diamine to block maximal electroshock-iniduced seizures (MES) was determined according to the method above.

$N^3$-[4-(4-Fluorophenoxy)benzyl]pyridine-2,3-diamine was injected i.v. to mice 15 minutes before the test procedure. The compound exhibited protection against MES with an ED$_{50}$ (the dose protecting 50% of animals) of 0 mg/kg.

$N^3$-[4-(3-Fluorobenzyloxy)benzyl]pyridine-2,3-diamine was tested similarly and it exhibited protection against MES with an ED$_{50}$ of 2.9 mg/kg.

EXAMPLE 4

Activity of N³-[4-(4-fluorophenoxy)benzyl] pyridine-2,3-diamine as Sodium Channel Blocker N³-[4-(4-Fluorophenoxy)benzyl]pyridine-2,3-diamine was tested in the electrophysiological and binding assays as described above and produced dose-dependent inhibition of voltage-gated sodium currents recorded in HEK-293 cells stably expressing the hSKMI isoform of Na⁺ channels. The blocking effect of this compound on Na⁺ currents was highly sensitive to the holding voltage, indicating that N³-[4-(4-fluorophenoxy)benzyl]pyridine-2,3-diamine binds to voltage-sensitive Na⁺ channels in their inactivated states and has weak potency towards Na⁺ channels in their resting states (Ragsdale el col., *Mol. Pharmacol.* 40:756–765 (1991), Kuo and Beans, *Mol. Pharmacol.* 46:716–725 (1994)). The apparent antagonist dissociation constant $K_i$ (the concentration of a compound that produces half maximal inhibition) of this compound for inactivated sodium channels is 0.06 μM.

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:

1. A compound having the Formula I:

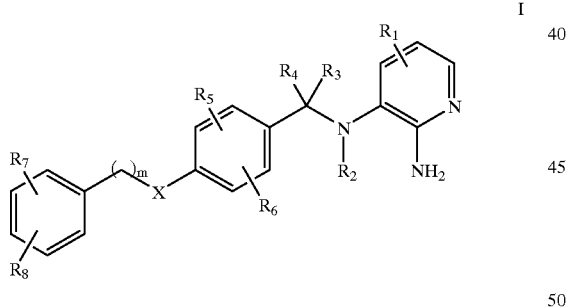

or a pharmaceutically acceptable salt, prodrug or solvate thereof, wherein:

$R_1$ is selected from the group consisting of hydrogen, alkyl, alkenyl, alkynyl, halogen, haloalkyl, cycloalkyl, amino, aminoalkyl hydroxyalkyl, alkoxyalkyl, alkoxy, alkylthio, alkylsulfinyl, alkylsulfoniyl, carboxyalkyl, cyano, alkylamino, aminocarbonyl, alkylaminocarbonyl, arylaminocarbonyl, aralkylaminocarbonyl, alkylcarbonylamino, arylcarbonylamino, alkylcarbonyl, heterocyclocarbonyl, aminosulfdnyl, alkylaminostilfonyl, and heterocyclosulfonyl, all of which can be optionally substituted;

$R_2$ is hydrogen or $C_{1-6}$ alkyl and $R_3$ is hydrogen, or $R_2$ and $R_3$ together form a bond;

$R_4$ is hydrogen or $C_{1-6}$ alkyl;

$R_5$, $R_6$, $R_7$, and $R_8$ are independently selected from the (group consisting of hydrogen, alkyl, alkenyl, alkynyl, halogen, haloalkyl, hydroxyalkyl, hydroxy, nitro, amino, aminoalkyl, cyano, amide, carboxyalkyl, alkoxyalkyl, ureido, acylamino, thiol, acyloxy, azido, alkoxy, carboxy, carbonylamido and alkylthiol;

X is one of O, S, $NR_9$, or $CH_2$, wherein $R_9$ is hydrogen or alkyl; and m is 0–3.

2. The compound of claim 1, wherein $R_1$ is selected from the group consisting of independently selected from the group consisting of hydrogen, $C_1$–$C_6$ alkyl, $C_2$–$C_6$ alkenyl, $C_2$–$C_6$ alkynyl, amino($C_1$–$C_6$)alkyl, amino, $C_1$–$C_6$ alkylthio, cyano, $C_1$–$C_6$ alkylsulfinyl, hydroxy($C_1$–$C_6$)alkyl, $C_1$–$C_6$ alkoxy, aminocarbonyl, $C_1$–$C_6$ alkylaminocarbonyl, $C_6$–$C_{10}$ arylaminocarbonyl, $C_6$–$C_{10}$ aryl($C_1$–$C_6$) alkylamino-carbonyl, $C_1$–$C_6$ alkylcarbonylamino, $C_6$–$C_{10}$ arylcarbonylamino, $C_6$–$C_{10}$ aryl($C_1$–$C_6$) alkylcarbonylamino, $C_1$–$C_6$ alkylcarbonyl, heterocyclocarbonyl, aminosulfonyl, $C_1$–$C_6$ alkylaminosulfonyl, $C_1$–$C_6$ alkylsulfonyl, and heterocyclosulfonyl.

3. The compound of claim 2, wherein $R_1$ is selected from the group consisting of hydrogen, $C_1$–$C_6$ alkyl, $C_1$–$C_6$ alkoxy, amino($C_1$–$C_6$)alkyl, $C_1$–$C_6$ alkylthio and aminocarbonyl.

4. The compound of claim 1, wherein $R_5$, $R_6$, $R_7$, and $R_8$ are independently selected from the group consisting of hydrogen, halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$)alkyl, $C_6$–$C_{10}$ aryl($C_2$–$C_6$)alkenyl, $C_6$–$C_{10}$ aryl($C_2$–$C_6$)alkynyl, $C_1$–$C_6$ hydroxyalkyl, nitro, amino, ureido, cyano, $C_1$–$C_6$ acylamido, hydroxy, thiol, $C_1$–$C_6$ acyloxy, azido, $C_1$–$C_6$ alkoxy, or carboxy.

5. The compound of claim 4, wherein $R_5$ and $R_6$ are both hydrogen, $R_7$ is hydrogen and $R_8$ is a fluoro in the meta- or para-position.

6. The compound of claim 1, wherein X is O or S.

7. The compound of claim 6, wherein X is O.

8. The compound of claim 1, having the Formula II:

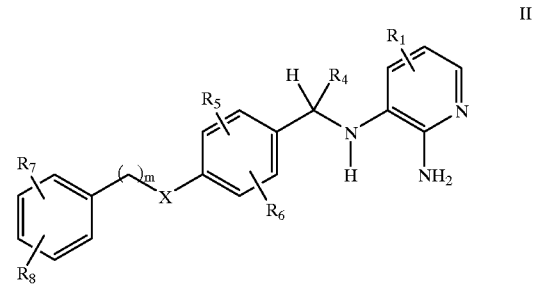

wherein $R_1$, $R_4$, and $R_5$–$R_8$ are as defined in claim 1, X is O or S and m is 0 or 1.

9. The compound of claim 8, wherein $R_1$ is selected from the group consisting of hydrogen, $C_1$–$C_6$ alkyl, $C_2$–$C_6$ alkenyl, $C_2$–$C_6$ alkynyl, amino($C_1$–$C_6$)alkyl, amino, $C_1$–$C_6$ alkylthio, cyano, $C_1$–$C_6$ alkylsulfinyl, hydroxy($C_1$–$C_6$)alkyl, $C_1$–$C_6$ alkoxy, aminocarbonyl, $C_1$–$C_6$ alkylaminocarbonyl, $C_6$–$C_{10}$ arylaminocarbonyl, $C_6$–$C_{10}$ aryl($C_1$–$C_6$) alkylamino-carbonyl, $C_1$–$C_6$ alkylcarbonylamino, $C_6$–$C_{10}$ arylcarbonylamino, $C_6$–$C_{10}$ aryl($C_1$–$C_6$) alkylcarbonylamino, $C_1$–$C_6$ alkylcarbonyl, heterocyclocarbonyl, aminosulfonyl, $C_1$–$C_6$ alkylaminosulfonyl, $C_1$–$C_6$ alkylsulfonyl, and heterocyclosulfonyl.

10. The compound of claim 9, wherein $R_1$ is selected from the group consisting of hydrogen, $C_1$–$C_6$ alkyl, $C_1$–$C_6$ alkoxy, amino($C_1$–$C_6$)alkyl, $C_1$–$C_6$ alkylthio and aminocarbonyl.

11. The compound of claim 1, wherein $R_5$, $R_6$, $R_7$, and $R_8$ are independently selected from the group consisting of hydrogen, halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$)alkyl, $C_6$–$C_{10}$ aryl($C_2$–$C_6$)alkenyl, $C_6$–$C_{10}$ aryl($C_2$–$C_6$)alkynyl, $C_1$–$C_6$ hydroxyalkyl, nitro, amino, ureido, cyano, $C_1$–$C_6$ acylamido, hydroxy, thiol, $C_1$–$C_6$ acyloxy, azido, $C_1$–$C_6$ alkoxy, or carboxy.

12. The compound of claim 11, wherein $R_5$ and $R_6$ are both hydrogen, $R_7$ is hydrogen and $R_8$ is a fluoro in the meta- or para-position.

13. The compound of claim 1, wherein said compound is:

$N^3$-[4-(3-fluorobenzyloxy)benzyl]pyridine-2,3-diamine;

$N^3$-[4-(3-fluorobenzyloxy)benzylidene]pyridine-2,3-diamine;

$N^3$-[4-(4-fluorophenoxy)benzyl]pyridine-2,3-diamine; or $N^3$-[4-(4-fluorophenoxy)benzylidene]pyridine-2,3-diamine;

or a pharmaceutically acceptable salt, prodrug or solvate thereof.

14. A pharmaceutical composition, comprising a compound of claim 1 and a pharmaceutically acceptable carrier or diluent.

15. A method of treating a disorder responsive to the blockade of sodium channels in a mammal suffering therefrom, comprising administering to a mammal in need of such treatment an effective amount of a compound of claim 1 or a pharmaceutically acceptable salt, prodrug or solvate thereof.

16. A method for treating, preventing or ameliorating neuronal loss following global and focal ischemia; treating, preventing or ameliorating neurodegenerative conditions; treating, preventing or ameliorating pain or tinnitus; treating, preventing or ameliorating manic depression; providing local anesthesia; or treating arrhythmias, or treating convulsions, comprising administering to a mammal in need of such treatment an effective amount of a compound of claim 1 or a pharmaceutically acceptable salt, prodrug or solvate thereof.

17. The method of claim 16, wherein the method is for treating, preventing or ameliorating pain and said pain is one of neuropathic pain, surgical pain or chronic pain.

18. A method of alleviating or preventing seizure activity in an animal subject, comprising administering to said animal in need of such treatment an effective amount of a compound of claim 1 or a pharmaceutically acceptable salt, prodrug or solvate thereof.

19. A compound of claim 1, wherein said compound is $^3$H or $^{14}$C radiolabeled.

* * * * *

UNITED STATES PATENT AND TRADEMARK OFFICE
CERTIFICATE OF CORRECTION

PATENT NO. : 6,335,354 B2  Page 1 of 1
DATED : January 1, 2002
INVENTOR(S) : Derk J. Hogenkamp It is certified that error appears in the above-identified patent and that said Letters Patent is hereby corrected as shown below:

<u>Column 4,</u>
Line 50-51, please delete "$N^3$-[4-(3-fluorobenzyloxy)benzyl]denelpyridine-2,3-diamine" and enter therefor -- $N^3$-[4-(3-fluorobenzyloxy)benzylidene]pyridine-2,3-diamine --.

<u>Column 15,</u>
Line 57, please delete "alkylsulfoniyl" and enter therefor -- alkylsulfonyl --.
Line 62, please delete "aminosulfdnyl" and enter therefor -- aminosulfonyl --.
Line 63, please delete "alkylaminostilfonyl" and enter therefor -- alkylaminosulfonyl --.

<u>Column 16,</u>
Line 2, please delete "(group" and insert therefor -- group --.
Lines 11-12, please delete "independently selected from the group consisting of".

Signed and Sealed this

Twentieth Day of August, 2002

*Attest:*

JAMES E. ROGAN
*Director of the United States Patent and Trademark Office*

*Attesting Officer*